United States Patent [19]
Greenhut

[11] Patent Number: 5,365,932
[45] Date of Patent: Nov. 22, 1994

[54] CARDIAC SIGNAL SENSING DEVICE HAVING SENSITIVITY AUTOMATICALLY CONTROLLED IN RESPONSE TO METABOLIC DEMAND

[75] Inventor: Saul E. Greenhut, Aurora, Colo.

[73] Assignee: Telectronics Pacing System, Inc., Englewood, Colo.

[21] Appl. No.: 116,135

[22] Filed: Sep. 2, 1993

[51] Int. Cl.$^5$ .......................................... A51B 5/0428
[52] U.S. Cl. ................................................... 128/696
[58] Field of Search ................ 128/696, 700, 706, 708

[56] References Cited

U.S. PATENT DOCUMENTS

| | | | |
|---|---|---|---|
| 4,325,384 | 4/1982 | Blaser et al. | 128/696 |
| 4,617,938 | 10/1986 | Shimoni et al. | 128/208 |
| 4,692,719 | 9/1987 | Whigham | 332/11 |
| 4,702,253 | 10/1987 | Nappholz et al. | 128/419 PG |
| 4,708,144 | 11/1987 | Hamilton et al. | 128/419 PG |
| 4,779,617 | 10/1988 | Whigham | 128/419 PG |
| 4,821,724 | 4/1989 | Whigham et al. | 128/419 PG |
| 4,901,725 | 2/1990 | Nappholz et al. | 128/419 PG |
| 4,903,700 | 2/1990 | Whigham et al. | 128/419 PG |

OTHER PUBLICATIONS

Levine, P. A. et al., "A Guide to Cardiac Pacing for Optimum Hemodynamic Benefit", Mt. Kisco, N.Y., Futura Publishing Co., pp. 22–26 (1983).

Frohlig, E. et al., "Atrial Sensing Performance of AV Universal Pacemakers During Exercise . . . ", PACE 1988; 11:47–60.

Bricker, T. J. et al., "Decrease in Canine Endocardial and Epicardial Electrogram Voltages with Exercise . . . " PACE, vol. 11, pp. 460–464 (1988).

Frohlig, G. et al., "Atrial Signal Variations and Pacemaker Malsensing During Exercise . . . ", J. Am. Coll. Cardiology 1988; 11:806–13.

Sutton, R. et al., "The Foundations of Cardiac Pacing, Part 1 . . . ", Mt. Kisco, N.Y., Futura Publishing Co., p. 7 (1991).

Primary Examiner—William E. Kamm
Attorney, Agent, or Firm—Gottlieb, Rackman & Reisman

[57] ABSTRACT

A pacemaker automatically adjusts sensitivity as a function of metabolic demand. The amplitude of cardiac signals is naturally reduced during exercise. The pacemaker measures a physiological parameter to determine the patient's metabolic demand. In response to increases in the patient's metabolic demand the sensitivity is increased and in response to decreases in the patient's metabolic demand the sensitivity is decreased.

16 Claims, 4 Drawing Sheets

CARDIAC SIGNAL SENSING DEVICE HAVING SENSITIVITY AUTOMATICALLY CONTROLLED IN RESPONSE TO METABOLIC DEMAND

TECHNICAL FIELD

This invention relates to implantable devices for cardiac signal sensing and stimulation and, more particularly, to such devices having a capability to automatically adjust their sensitivities to changing cardiac electrical signal levels.

BACKGROUND ART

Problems in implanted pacemakers sensing heartbeats during periods of exercise have been found to occur in patients. Exercise has been found to cause a decrease in the amplitude of cardiac signals. This finding has been confirmed by measurements of endocardial and epicardial electrograms.

In cardiac pacing, "sensitivity" is the minimum amplitude of an input signal that will cause a pacemaker to respond. A cardiac event is sensed when the amplified input signal corresponding to that event exceeds a threshold level. If the sensitivity is too low, which occurs when the amplifier gain is too low or the sensing threshold level is too high, then some cardiac events will not be sensed because even their peak signals may not exceed the threshold level. However, if the sensitivity is too high, then the high gain of the amplifier or the low threshold level may result in background noise signals causing spurious sensing of cardiac events. Generally, in prior art pacemakers, the attending physician sets the sensitivity while monitoring the amplitude of cardiac signal waveforms. The physician sets the amplifier gain so that a particular maximum cardiac signal amplitude, characteristic of a sensed heartbeat, is attained. Then the background noise level is monitored and the sensing threshold is set between the background noise amplitude and the maximum cardiac signal amplitude. The difference between the sensing threshold and the amplitude of a heartbeat signal is called the "margin".

Because cardiac signal amplitudes are reduced when a patient exercises, changes in cardiac signal amplitude due to such exercise may lead to an incorrect sensitivity setting. Various studies have shown that the respective amplitudes of cardiac electrical signals decrease during exercise. Bricker, J. T. et al., "Decrease in Canine Endocardial and Epicardial Electrogram Voltages with Exercise: Implications for Pacemaker Sensing", *PACE,* Vol. 11, pages 460–464 (1988), relates the results of exercise tests showing that unfiltered electrogram amplitudes are decreased in 84% of test cases. Furthermore, Frohlig, G. et al., "Atrial Sensing Performance of AV Universal Pacemakers During Exercise" *PACE,* Vol. 11 pages 47–60 (1988), shows that 25 of 57 (44%) dual-chamber pacemakers exhibited poor atrial sensing during exercise by the patients. Proper atrial sensing resumed in 16 of the 25 pacemakers within 1 to 7 minutes following the cessation of such exercise. In the remaining pacemakers, the atrial sensing threshold generally was decreased by one-half with normal sensing. Frohlig, G. et al., "Atrial Signal Variations and Pacemaker Malsensing During Exercise: A Study in the Time and Frequency Domain", *Journal of the American College of Cardiology,* Vol. 11, pages 806–813 (1988), went on to measure atrial signal variability in the time and frequency domains. Unfiltered atrial electrograms (AEGMs) from 33 patients were telemetered from an implanted pacemaker to an external monitoring computer. On the average, atrial electrocardiogram amplitudes decreased by 11% while AEGM amplitudes decreased by 11–49% in 45% of patients.

The problem of undersensing of cardiac signals during exercise is insidious for cardiac pacemaker patients who are young or athletic and whose pacemakers function in the DDD or DDDR pacing mode. In these modes (hereafter referred to as collectively as DDDX) with a normally functioning sinus node, the pacing rate is set by the rate of natural atrial heartbeats. In the DDDX pacing mode, a correctly functioning sinus node hastens the rate of atrial heartbeats in response to the onset of exercise. The DDDX pacer senses an atrial heartbeat, waits a predetermined "A-V delay" period and, unless a natural ventricular heartbeat is sensed during this period, upon the lapse of this period, delivers a pacing pulse to the ventricle. If, during exercise, the pacemaker fails to sense some or all natural atrial heartbeats (called P waves), ventricular pacing will not synchronously follow the true, natural rate of atrial heartbeats. Atrioventricular synchrony results in an augmentation of cardiac output and improved hemodynamics. [See, e.g., Levine, P. A., Mace R. C.: "Pacing Therapy: A Guide to Cardiac Pacing for Optimum Hemodynamic Benefit." Mount Kisco, N.Y., Futura Publishing Co., 1983, pp. 22–26.] It is also the only method for augmented rate increase in a DDD pacemaker.

Another hazard to a cardiac patient arises from the undersensing of atrial or ventricular cardiac signals. If a pacemaker fails to correctly sense atrial heartbeats (called P waves) or ventricular heartbeats (called R waves), the pacemaker, rather than sensing a true, i.e., natural, P or R wave and correctly inhibiting delivery of a pacing pulse to the atrium or ventricle, may erroneously deliver a pacing pulse during the repolarization of the respective chamber of the heart. Pacing during heart repolarization, particularly during the "relative refractory period" of the heart, which is known as the heart's vulnerable period, can induce an atrial or ventricular fibrillation, depending upon the chamber of origin. Ventricular fibrillation results in cardiac arrest and death without intervention. [See, e.g., Sutton R., Bourgeois I.: "The Foundations of Cardiac Pacing, Part I: An Illustrated Practical Guide To Basic Pacing." Mount Kisco, N.Y., Futura Publishing Co., 1991, p. 17.]

An additional hazard to a pacemaker patient may result from the oversensing of atrial or ventricular depolarizations. Oversensing refers to the sensing of non-atrial or non-ventricular depolarizations (e.g., electromagnetic interference, cardiac repolarization, far-field depolarization from the opposing chamber, or myopotentials). Oversensing in the atrium in a DDDX pacemaker can cause rapid ventricular pacing or the false activation of atrial upper rate behaviors. Oversensing in the ventricle can cause inhibition of ventricular output or noise reversion pacing. Ventricular inhibition could cause ventricular rates to decrease, such that the patient experiences dizziness, syncope, or cardiac standstill leading to cardiac arrest.

The operation of automatically adjusting sensitivity, by modifications to amplifier gain and to sensing threshold, has been performed in prior art pacemakers on the basis of measurements of sensed cardiac signals alone. For example, U.S. Pat. No. 4,708,144, entitled "Automatic Sensitivity Control for a Pacemaker" issued Nov. 24, 1987 to J. R. Hamilton et al., teaches an implantable pacemaker in which the sensitivity of the sense channel is automatically controlled. The peak amplitude of each R wave is measured and a long-term average is derived. The gain of the sense channel is adjusted automatically in accordance with the average of the measured peak values.

If noise voltages are present at the electrodes, then a cardiac stimulator may erroneously treat such noise as a natural heartbeat and fail to stimulate the heart when needed even though no natural heartbeat has actually occurred. Thus it is important that there be a way to discriminate between noise and a heartbeat. Noise rejection in prior art pacemakers has generally involved the making of adjustments to the pacemaker sensing threshold parameter. The "sensing threshold" is the amplitude of a sensed or input signal which is just sufficient to cause the pacemaker to recognize the respective cardiac event. By raising the sensing threshold, the effect of the noise is reduced. U.S. Pat. No. 4,779,617, entitled "Pacemaker Noise Rejection System", issued to R. H. Whigham on Oct. 25, 1988, discloses a noise rejection circuit for an implantable pacemaker. During the "relative refractory period" (RRP), as defined by the pacemaker, following a ventricular heartbeat, the pacemaker senses the peak noise amplitude. The pacemaker RRP is restarted whenever the sensed noise amplitude exceeds the previous peak noise amplitude. Following the lapse of the RRP, the peak detected amplitude, representing the noise signal, is added to the programmed threshold amplitude, and the sum thereof is used as the threshold amplitude for heartbeat sensing.

It is an object of the present invention to improve the accuracy of cardiac signal sensing when a patient is exercising.

An object of the present invention is to automatically set the sensitivity of a pacemaker as a function of a physiological sensor measurement.

An additional object of the present invention is to automatically set the sensitivity of a pacemaker as a function of both a physiological sensor measurement and the characteristics of sensed cardiac electrical signals.

It is also an object of the present invention to automatically set the sensitivity of a pacemaker as a function of a physiological sensor measurement by making adjustments to a sensing threshold parameter, an amplifier gain parameter or both parameters.

It is a further object of the invention to automatically adjust sensing sensitivity, particularly in the atrial channel, of a dual chamber pacemaker operating in a DDD mode, so that A-V synchronous pacing is provided when a patient is exercising.

A feature of the present invention is a pacemaker which automatically adjusts for the relatively lower amplitude cardiac signals which occur while a patient is exercising so that the pacemaker may employ a smaller sensing threshold safety margin than is otherwise programmable or otherwise automatically determined, based on the characteristics of the cardiac electrical signal alone, resulting in minimized oversensing of myopotentials and other electrical noise. Also, in the instance in which the sensing threshold was programmed with too small a sensing threshold safety margin, the present invention will prevent undersensing, i.e., loss of capture, of the cardiac signal during exercise.

SUMMARY OF THE INVENTION

In accordance with the principles of the present invention, a patient-implantable, heartbeat sensing, apparatus includes a sensor for measuring a physiological parameter, and a means for determining the patient's metabolic demand from this physiological parameter. In addition to the physiological parameter sensor, the apparatus includes (i) a cardiac signal sensor for sensing a signal responsive to both cardiac electrical activity and noise, (ii) means for analyzing the output signal from the cardiac signal sensor and determining if and when a natural heartbeat has occurred, and (iii) means for adjusting the sensitivity of said analyzing and determining means. A controller automatically sets the sensitivity adjusting means. The controller responds to increases in the patient's metabolic demand by increasing the sensitivity, and responds to decreases in the patient's metabolic demand by decreasing the sensitivity.

Sensitivity adjustments may be provided by setting a sensing threshold level, an amplifier gain amplitude, or both. The apparatus also may provide for the sensitivity adjusting means to include a comparator for comparing the amplitudes of signals from the cardiac signal sensor against a sensing threshold level for determining the occurrence of a natural heartbeat. In this case, the controller automatically sets the sensing threshold level. The controller responds to increases in the patient's metabolic demand, and the concomitant decrease in the heartbeat signal amplitude, by decreasing the sensing threshold level; and responds to decreases in the patient's metabolic demand, and the concomitant increase or restoration of the heartbeat signal amplitude, by increasing the sensing threshold level.

In one embodiment, the controller may vary the sensitivity using a variable sensing threshold level, by a function of the metabolic parameter alone. If the cardiac signal amplitude exceeds the variable sensing threshold level during the heartbeat sensing period, then the apparatus determines that a natural heartbeat has occurred.

In a second embodiment, the controller may vary the sensitivity using a variable sensing threshold level, by (i) measuring the peak amplitude of the cardiac signal in response to the detection of a natural heartbeat by the analyzing and determining means, and (ii) deriving a level which is representative of the average of the measured peak amplitudes during a preceding time interval which is pre-determined to be at least a few cardiac cycles long. The controller then sets the variable sensing threshold level to an initial threshold level in response to the sensing of the occurrence of a heartbeat and times a retriggerable relative refractory period (RRP). If during the duration of the RRP, the apparatus detects a cardiac signal having an amplitude greater than the variable sensing threshold level, the controller retriggers the RRP period and increases the variable sensing threshold level. Upon the lapse of that current RRP during which the cardiac signal amplitude has not exceeded the variable sensing threshold level, the controller initiates a heartbeat sensing period and sets a variable sensing threshold level as a function of one or more of: (i) the variable sensing threshold level at the end of the preceding RRP, (ii) the average measured peak amplitude, and (iii) the patient's metabolic demand. If the cardiac signal amplitude exceeds the variable sensing threshold level during the heartbeat sensing period, then the apparatus determines that a natural heartbeat has occurred.

In a similar embodiment, the controller may again vary the sensitivity using a variable sensing threshold level by (i) measuring the peak amplitude of the cardiac signal in response to the detection of a natural heartbeat by the analyzing and determining means, and (ii) deriving a level which is representative of the average of the measured peak amplitudes during a preceding time period which is pre-determined to be at least a few cardiac cycles long. The controller may then set the variable sensing threshold level to an initial threshold level in response to sensing the occurrence of a heartbeat and successively increase the threshold level to a final level as the amplitude of the sensed cardiac signal increases until a final threshold level is reached which represents the noise level in the cardiac signal. When the apparatus finds the final threshold level, the controller initiates a heartbeat sensing period and sets a variable sensing threshold level as a function of one or more of: (i) the variable sensing threshold amplitude at the end of the preceding RRP, (ii) the average measured peak amplitude, and (iii) the patient's metabolic demand. If the cardiac signal amplitude exceeds the variable sensing threshold level during the heartbeat sensing period, then the apparatus determines that a natural heartbeat has occurred.

If no heartbeat senses are counted for a given time period (e.g., 1 minute) while metabolic demand is at a level greater than resting, there may be a mode of operation in which the sensing threshold of the pacemaker is decreased for a given time period (e.g., 10 sec) in order to search for intrinsic cardiac activation. The sensing threshold may then be permanently adjusted downward for this patient if sensing occurs during this search period.

BRIEF DESCRIPTION OF THE DRAWING

Further objects, features and advantages of the invention will become apparent upon consideration of the following detailed description in conjunction with the drawing, in which.

DESCRIPTION OF THE INVENTION

Figure 1:
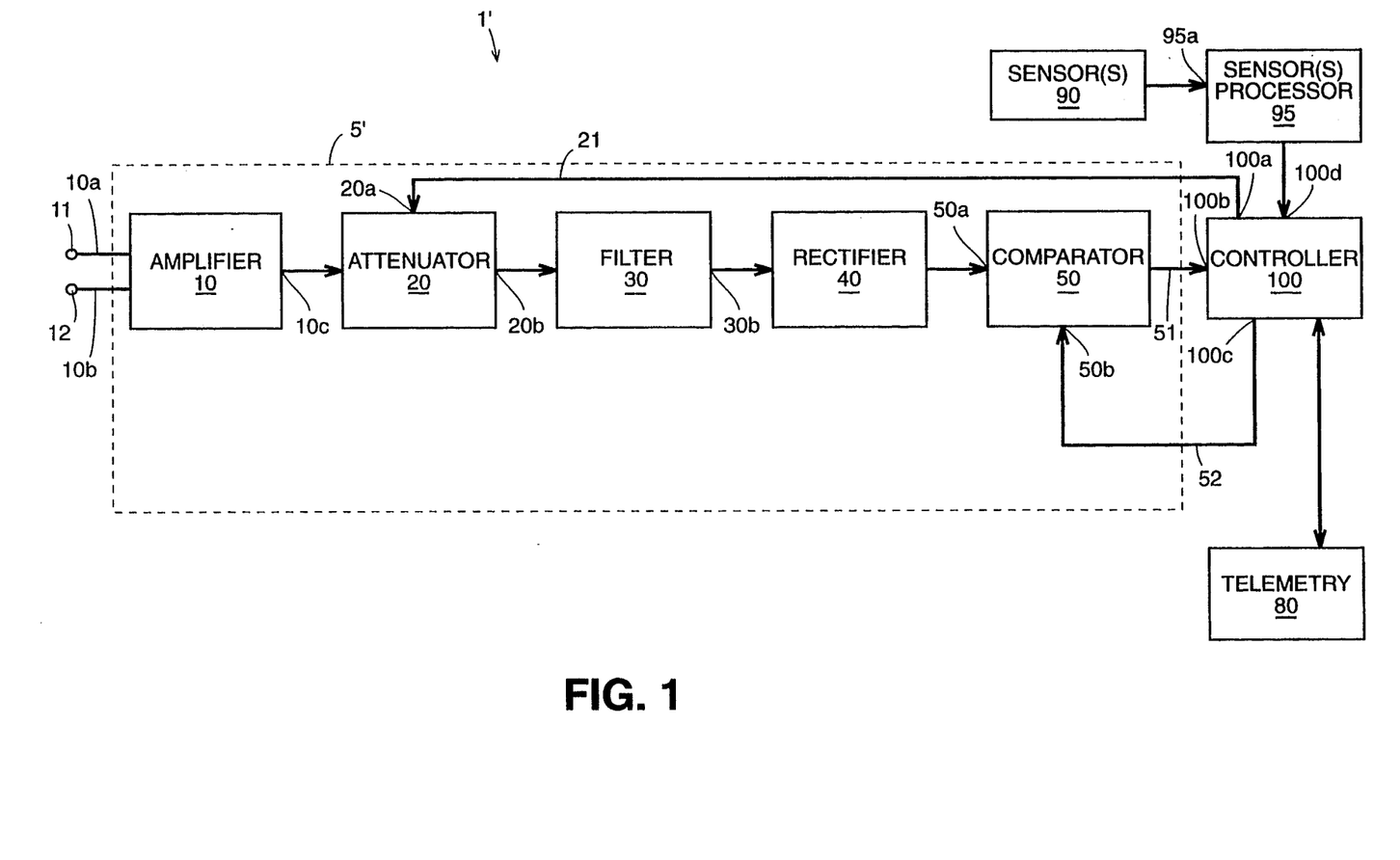
FIG. 1 depicts a schematic block diagram of a heartbeat sensing apparatus of the preferred embodiment of the invention, (without peak detection circuitry,) including a sensing circuit.

FIG. 1 is a block diagram of the preferred embodiment of the invention and shows the circuit elements of a cardiac signal sensing device such as a pacemaker 1', which may be implanted in a patient, and which has a cardiac signal sensing channel 5'. Only components related to sensing are included in FIG. 1. A cardiac electrical signal voltage is sensed between an anode 11 and a tip electrode (cathode) 12 of a pair of respective conductors 10a, 10b, and is amplified by a sensing amplifier 10 which is provided for monitoring cardiac activity. An attenuator 20 is coupled to the output 10c of the amplifier 10. A gain control conductor 21 couples one output 100a of a controller 100 to an input 20a of the attenuator 20 to provide for the control of the input signal gain. The output 20b of the attenuator 20 is coupled to the input of a filter 30. The filter is a conventional band-pass filter to filter the cardiac signal so that frequencies of primarily cardiac interest remain. A typical filter circuit has a center frequency of 44 Hz and a value of Q of 2. The output 30b of the filter is coupled to the input of a rectifier 40. The rectifier effectively takes the absolute value of the signal 30b and produces an output 50a to a signal comparator 50. The comparator 50 determines whether the signal at its input 50a from the rectifier 40 is greater than the threshold of the comparator 50. The threshold of the comparator is set by the input line 50b from the output of the controller 100c. When the rectified cardiac signal at input 50a is greater than the threshold of the comparator 50, typically when an R wave is sensed, an output signal is provided on a sense output line 51. This signal, transmitted over the sense output line 51 to the input 100b of the controller 100, indicates that a heartbeat has been sensed. The rectifier 40 is present because, depending upon the placement of the lead(s), the R wave can have a greater excursion in either the plus or minus direction at the output 30b of the filter 30. To best reject noise, the threshold value should be set as high as possible. To set the threshold as high as possible, it is desirable to initiate a cardiac sense signal upon the largest change in magnitude, also called the slope or derivative, of the raw cardiac signal input voltage across the electrodes 11 and 12, regardless of the sign or polarity of this cardiac signal voltage. The filter 30 effectively performs this differentiation.

The controller 100 is a microcontroller or microprocessor which is deactivated, to conserve the power supply, for most of each pacing cycle, while waiting for an event, such as a cardiac electrical signal or the lapse of a delay period. A signal on the line 51 from the comparator to the controller sense input 100b is an activation signal for the controller 100 indicating a possible natural heartbeat event.

A single sensor (or multiple sensors) 90 is provided for sensing a physiological variable of any appropriate known type, such as respiratory minute volume, respiration rate, paced depolarization integral patient activity, QT interval, central venous blood temperature, blood oxygen saturation, blood pH and others. The type of sensor or sensors used is not critical to the present invention. Appropriate sensors are any which are capable of producing a signal which varies predictably as a patient's metabolic demand varies under conditions of exercise or other stress. The sensor or sensors 90 generates a signal which is coupled to the input 95a of a sensor or sensors processor 95 where it is then processed and applied to the input 100d of the controller 100, which may use this information for various purposes. The controller uses the input 100d to adjust the comparator threshold via line 52 or the signal gain via line 21. In the preferred embodiment of the invention, a minute volume sensor is provided to measure a patient's metabolic demand. Although the scope of the invention does not require that the sensor 90 measurement and metabolic demand derivation operations be used for any purpose other than for automatically setting gain or sensitivity, it is obvious that these operations may be employed to set other operational parameters, such as the pacing rate. Two examples of sensors and processing systems for measuring minute volume and deriving metabolic indicator values are disclosed in U.S. Pat. No. 4,702,253, entitled "Metabolic-Demand Pacemaker and Method of Using the Same to Determine Minute Volume", issued to T. A. Nappholz et al. on Oct. 27, 1987, and U.S. Pat. No. 4,901,725, entitled "minute Volume Rate-Responsive Pacemaker", issued to T. A. Nappholz et al. on Feb. 20, 1990. These patents are hereby incorporated by references.

The pacemaker 1' includes a telemetry circuit 80, which is conventional in the art of implantable cardiac stimulation devices, so that information may be exchanged between the pacemaker 1' and an external programming device (not shown).

Embodiments of the present invention may automatically adjust sensitivity by one or more methods as a function of a patient's metabolic demand. In a first example, the pacemaker 1' may be programmed by an external programming device via the telemetry circuit 80 to set a gain control value Y at the input 20a and a threshold control value X at input 50b which are standard for the patient at rest. Furthermore, the programming may specify that the sense threshold control value X decrease by an amount proportional to the measured metabolic demand indicator value. For example, if the signal from the rectifier 40 is in the range of 0.5 mV to 25.0 mV and if the normal, resting sense threshold value is 2 mV, then the automatically adjusted sense threshold may be modified, possibly to range in a linear manner between a low limit (e.g., 1.5 mV during strenuous exercise) and a high limit (e.g., 2.2 mV during sleep) as a function of the patient's metabolic demand. The function relating the metabolic demand indicator value to the change in sensing threshold value, may be other than linear, depending on the needs of the patient.

In a second example, the pacemaker 1' may be programmed by an external programming device via the telemetry circuit 80 to set a gain control value Y and a threshold control value X which are standard for the patient at rest. Furthermore, the programming may specify that the amplifier gain control value Y increase by an amount proportional to the measured demand indicator value. For example, if the gain control value Y can vary such that, for a given sensing threshold value X, the sensitivity varies in the range from 0.5 mV to 25.0 mV and the normal sensitivity is 2.0 mV, the automatically adjusted gain control value 21 parameter may be changed, possibly to range in a linear manner to provide a sensitivity between a low limit (e.g. 1.5 mV during exercise) and a high limit (e.g., 2.2 mV during sleep) as a function of the patient's metabolic demand. The function relating the metabolic demand indicator to the change in gain control may be other than linear, depending on the needs of the patient.

The measurement of the resting sense threshold value is standard in the treatment of pacemaker patients and is performed by varying the sense threshold via telemetry and determining the value at which sensing is lost. The value of the peak exercise sensing threshold could be estimated, based upon pacemaker patient population averages or average change from resting level. The peak exercise sensing threshold could also be measured for the pacemaker patient by performing the standard, resting sense threshold measurement while the patient is exercising at peak levels. The pacemaker 1' may then be programmed by an external programming device via the telemetry circuit 80 to set either the gain or sensing threshold as in the manner of the two methods above. This time, however, the gain or sensing threshold is set for both rest and exercise and a linear (or other) relationship for gain or sensing threshold is established for levels of metabolic demand in between.

The improvement in cardiac signal sensing which is thereby achieved is shown in the following example: A prior art pacemaker may fail to sense a heartbeat during exercise because the threshold is set too high. The pacemaker of the present invention will decrement the sensing threshold based on changes in the patient's metabolic demand alone and, as a result, maintain appropriate sensing of natural heartbeats. Thus, the present invention allows the use of higher sensing thresholds which provide improved noise discrimination while continuing to sense true natural heartbeats.

Figure 2:
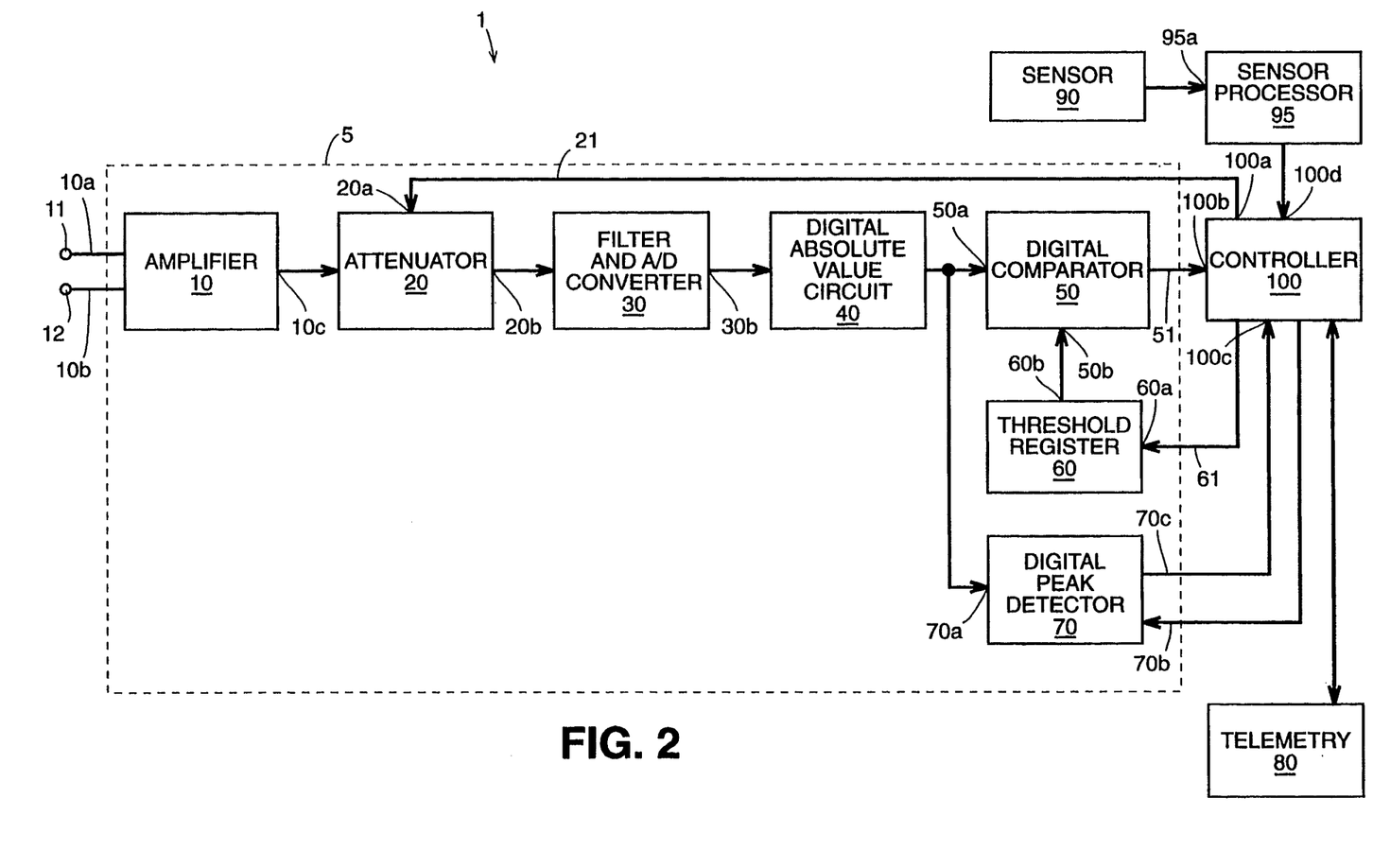
FIG. 2 a schematic block diagram of a heartbeat sensing apparatus of another embodiment of the invention (with peak detection circuitry,) including a sensing circuit.

FIG. 2 is a block diagram which shows the circuit elements of a more complex cardiac signal sensing device such as a pacemaker b, which has a cardiac signal sensing channel 5. A cardiac electrical signal voltage is sensed between an anode 11 and a tip electrode (cathode) 12 of a pair of respective conductors 10a, 10b, and is amplified by a sensing amplifier 10 which is provided for monitoring cardiac activity. An attenuator 20 is coupled to the output 10c of the amplifier be. A gain control conductor 21 couples one output 100a of a controller 100 to an input 20a of the attenuator 20 to provide for the control of the input signal gain. The output 20b of the attenuator 20 is coupled to the input of a combined filter and analog-to-digital converter 30. Particular circuitry for this filter-converter may be found in U.S. Pat. No. 4,903,700, entitled "Pacing Pulse Compensation" issued to R. H. Whigham et al. on Feb. 27, 1990; U.S. Pat. No. 4,821,724, entitled "Pacing Pulse Compensation" issued to R. H. Whigham et al on Apr. 18, 1989; and U.S. Pat. No. 4,692,719, entitled "Combined Pacemaker Delta Modulator and Bandpass Filter", issued to R. H. Whigham on Sep. 8, 1987. These patents are hereby incorporated by reference. The filter and A/D converter 30 serves as a conventional high-pass or bandpass filter to filter the cardiac signal so that only frequencies of cardiac interest remain, and also repeatedly derives a digital sample of the amplified and filtered analog cardiac sensed signal. A typical filter circuit for a cardiac pacemaker sensing circuit has a center frequency of about 44 Hz and a value of Q of 2. The output 30b of the filter-A/D converter is coupled to the input of a digital absolute value circuit 40. The circuit 40 determines the absolute value of the cardiac signal sensed on the electrodes 11 and 12 and furnished by the filter-A/D converter 30. Each digital sample from the absolute value circuit 40 advances to a first input 50a of a digital comparator 50. A second input 50b to the digital comparator 50 receives a threshold digital value from the output 60b of a threshold register 60. A threshold amplitude in digital form is set in the threshold register 60 by the controller 100 via a threshold control input 60a. The digital comparator 50 determines whether the signal at its input 50a from the digital absolute value circuit 40 is greater than the threshold digital value at its input 50b. When the absolute value of the cardiac signal at input 50a is greater than the threshold value at input 50b, typically when an R wave is sensed, an output signal is provided on a sense output line 51.

This signal, transmitted over the sense output line 51 to the input 100b of the controller 100, indicates that a heartbeat has been sensed. The reason that the absolute value circuit 40 uses the absolute value of the cardiac signal is that, depending on the placement of the leads, the R wave can have a greater excursion in either the plus or minus direction at the output 30b of the filter-A/D converter 30. To best reject noise, the threshold value should be set as high as possible. To set the threshold as high as possible, it is desirable to initiate a cardiac sense signal upon the largest change in magnitude, also called the slope or derivative, of the raw cardiac signal input voltage across the electrodes 11 and 12, regardless of the sign or polarity of this cardiac signal voltage.

Each digitized sample from the digital absolute value circuit 40 is also coupled to the input 70a of a digital peak detector 70. In response to a reset signal on input 70b from the controller 100, the largest of successive digital samples of the absolute value of the cardiac signal at the input 70a of the peak detector 70 is applied to the input 100c of the controller 100. Thus the controller 100 is provided with the largest sample which was sensed subsequent to the last reset signal pulse at input 70b.

In this embodiment of the invention, the controller 100 is a microcontroller or microprocessor which is deactivated, to conserve the power supply, for most of each pacing cycle, while waiting for an event, such as a cardiac electrical signal or the lapse of a delay period. A signal on the line 51 from the comparator to the controller sense input 100b is an activation signal for the controller 100 indicating a possible natural heartbeat event. Although the input signal across the electrodes 11 and 12 may change at such a rate that the comparator 50 is triggered, this does not necessarily imply that the last sample is the largest of the cardiac cycle. For this reason, the controller 100 delays sending a signal to the reset input 70b, e.g., for 30 milliseconds, following receipt of a signal on the sense input 100b. Only after 30 milliseconds have elapsed is the reset signal provided to the input 70b to reset the peak detector 70. During this time, an appropriate peak sample value should become available since a heartbeat peak signal, an R wave or P wave peak, normally follows the change in cardiac signal slope within 30 ms. Before resetting the peak detector 70, the controller 100 reads and stores the peak signal result via the peak input 100b.

A sensor (or multiple sensors) 90 is provided for sensing a physiological variable of any appropriate known type, such as respiratory minute volume, respiration rate, paced depolarization integral, patient activity, QT interval, central venous blood temperature, blood oxygen saturation, blood pH and others. The type of sensor or sensors used is not critical to the present invention. Appropriate sensors are any which are capable of producing a signal which varies predictably as a patient's metabolic demand varies under conditions of exercise or stress. The sensor or sensors 90 generates a signal which is coupled to the input 95a of a sensor or sensors processor 95, where it may be amplified, filtered and processed to derive a metabolic indicator digital value from the sensed physiological variable. An output from the sensor or sensors processor 95 is applied to the input 100d of the controller 100, which may use this information for various purposes. In this embodiment of the invention, a minute volume sensor is provided to measure a patient's metabolic demand. Although the scope of the invention does not require that the sensor or sensors 90 measurement and metabolic demand derivation operations be used for any purpose other than for automatically setting sensitivity, it is obvious that these operations may be employed to set other operational parameters, such as the pacing rate. Two examples of sensors and processing systems for measuring minute volume and deriving metabolic indicator values are disclosed in U.S. Pat. No. 4,702,253, entitled "Metabolic-Demand Pacemaker and Method of Using the Same to Determine Minute Volume", issued to T. A. Nappholz et al. on Oct. 27, 1987 and U.S. Pat. No. 4,901,725, entitled "Minute Volume Rate-Responsive Pacemaker" issued to T. A. Nappholz et al on Feb. 20, 1990. These patents are hereby incorporated by reference.

The pacemaker 1 includes a telemetry circuit which is conventional in the art of implantable cardiac stimulation devices, so that information may be exchanged between the pacemaker 1 and an external programming device (not shown).

Embodiments of the present invention may automatically adjust sensitivity by one or more methods as a function of a patient's metabolic demand. In a first example of FIG. 2, the pacemaker 1 may be programmed by an external programming device via the telemetry circuit 80 to set a gain control value Y at input 20a and a threshold control value X at input 60a which are standard for the patient at rest. Furthermore, the programming may specify that the sense threshold control value X decrease by an amount proportional to the measured metabolic demand indicator value. For example, if the samples from the digital absolute value circuit 40 can have values ranging from 0 through 31 and if the normal sense threshold value for appropriately distinguishing between noise and heartbeat signals is 7, then the automatically adjusted sense threshold level may be modified, possibly to range in a linear manner between a low limit (e.g., 3) and a high limit (e.g., 9) as a function of the patient's metabolic demand. The function relating the metabolic demand indicator value to the change in sensing threshold value, may be other than linear, depending on the needs of the patient.

In a second example, the pacemaker 1 may be programmed by an external programming device via the telemetry circuit 80 to set a gain control value Y and a threshold control value X which are standard for the patient at rest. Furthermore, the programming may specify that the amplifier gain control value Y increase by an amount proportional to the measured metabolic demand indicator value. For example, if the gain control value Y can vary such that, for a given sensing threshold value X, the sensitivity varies in the range from 0.5 mV to 25.0 mV and the normal sensitivity in the atria is 1.0 mV and the normal sensitivity in the ventricles is 2.0 mV, the automatically adjusted gain control value 21 parameter may be changed, possibly to range in a linear manner to provide a sensitivity between a low limit (e.g., 0.7 mV for atria and 1.5 mV for ventricles) and a high limit (e.g., 1.1 mV for atria and 2.2 mV for ventricles) as a function of the patient's metabolic demand. The function relating the metabolic demand indicator to the change in gain control value may be other than linear, depending on the needs of the patient.

In a third example, the sense threshold value X may be set via programming and the sensitivity may be set automatically via the following algorithm: The controller 100 adjusts the gain Y [gain is the inverse of sensitivity] in accordance with the average value of the peaks detected during successive cardiac cycles when signals from the sensor processor 95 analyzed by the controller 100 indicate that the patient is not exercising. The controller 100 updates the average value of the peak (AP) according to the following equation (1):

$$(NewAP) = (Z)*(OldAP) + (1-Z)*(NewSample). \quad (1)$$

where Z is a value between 0 and 1, NewAP is the updated value of the peak, OldAP is the value of the peak prior to updating and NewSample is the current peak value for the current cardiac cycle. There are many ways known in the art for deriving a long-term average, and the particular manner in which the average is computed is not important. What is important is that the new output, which is the gain control value Y provided to the attenuator 20, be a measure of the peak output value NewAP during at least the last several minutes. The larger the peak output value NewAP, the less amplification that is required for the sensed signal to exceed the threshold value. Thus, the larger the average value of the peaks, the greater is the attenuation and the less is the overall gain of the cardiac signal sensing channel 5. In this manner, the sensitivity of the sensing channel 5 is controlled as a function of the amplitude of the input signal voltage at the electrodes 11 and 12. Conventionally in prior art pacemakers, the attenuation level is set so that the peak output value amplitude is two to three times the threshold level. One of the reasons the margin is conventionally set so high is due to the change in cardiac signal amplitude during exercise. The operation of the present invention allows the margin to be set much lower, e.g., such that the peak output value NewAP is merely 50% greater than the threshold level. If the patient begins exercising and metabolic demand rises, then the controller 100 sets the sensitivity to increase by an amount which is proportional to the patient's increased metabolic demand.

Figure 3:
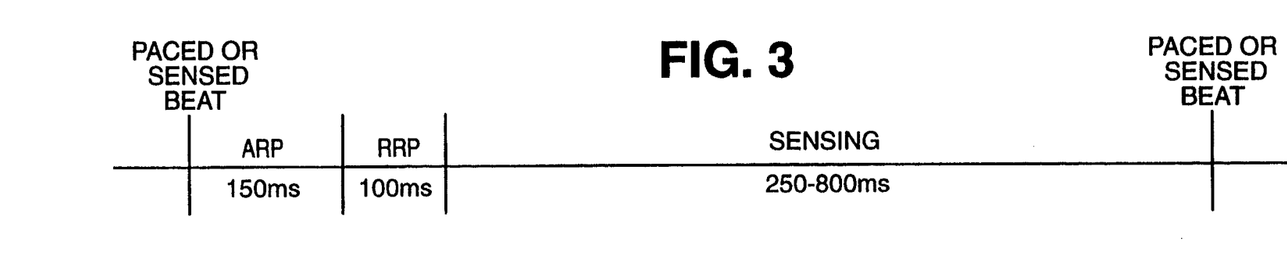
FIG. 3 depicts an absolute refractory period (ARP), a relative refractory period (RRP), and a sensing period with noise absent.
Figure 4:
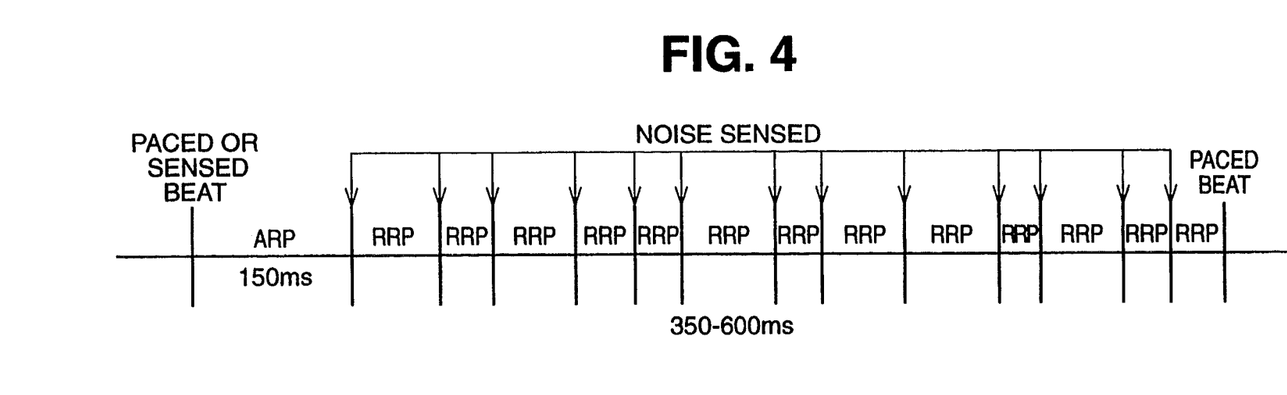
FIG. 4 depicts how an RRP is restarted whenever a noise signal is sensed during the preceding RRP.

In a fourth example, the sensitivity may be set via the programming; and the sense threshold value may be set automatically via the algorithm which follows. The operations of the automatic sense threshold procedure are best understood by making reference to a single cardiac cycle for the single cardiac signal sensing channel 5 shown in FIG. 3. The operations of the automatic sense threshold procedure are performed in both the atrial and ventricular channels. A natural absolute refractory period (ARP) follows each occurrence of either a pacing pulse initiated heartbeat or a natural heartbeat. That is, after the heartbeat which is caused by the depolarization wave of the heart's own pacemaker cells, and the remaining mass of cells, each of which depolarizes once its neighbor cell has been depolarized, there comes the recovery or repolarization of these cells. During this natural period (ARP), further depolarization is initially impossible, and the cell is refractory. During the natural ARP, which may continue for about 150 ms, the controller 100 times an equivalent period during which it disables the sensing function of the sensing channel 5. Thereafter, the controller 100 enables the sensing function and begins timing a period equivalent to the natural relative refractory period (RRP), lasting for about 100 ms, for example. During this period, it is possible for the cells to have sufficiently repolarized, and upon receiving a stronger than normal stimulus, to achieve another depolarization. If the amplified and filtered input signal from the electrodes 11 and 12 does not exceed the threshold control value stored in the threshold register 60 during the equivalent RRP, then, thereafter, the normal sensing function begins, in which a greater than threshold input signal level signifies a natural heartbeat. During this post ARP time, the controller 100 also times a machine cardiac cycle interval of a predetermined duration. If the cardiac cycle lapses before the sensing of a heartbeat, the controller 100 triggers the delivery of a pacing pulse to stimulate the ventricle contraction (heartbeat). If a greater than threshold signal voltage is sensed during the pacemaker RRP, it is considered to be the sensing of noise, rather than a heartbeat. FIG. 4 illustrates the operation of the controller 100 when noise is sensed during the pacemaker RRP. The sensing of noise during the RRP causes the controller 100 to time another machine RRP for a predetermined time (e.g., 100 ms). If noise is continuously present, as indicated in FIG. 4, then the controller 100 determines that this sensing indicates the presence of continuous noise and a pacing pulse is generated when the cardiac cycle times out, (i.e., lapses,) to ensure that the patient's ventricles contract.

Figure 5:
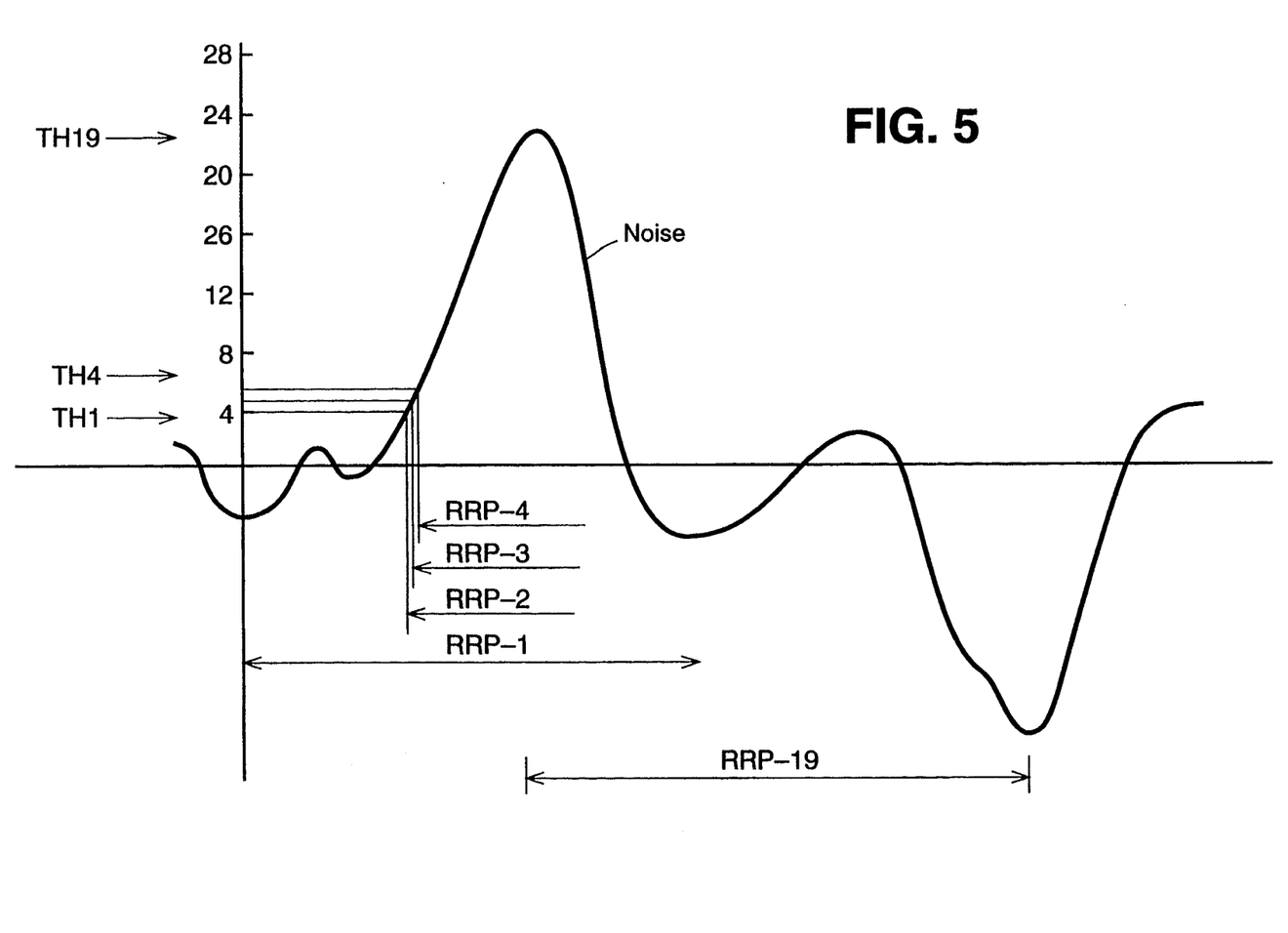
FIG. 5 depicts a noise signal which may be detected by the sensing circuit of the heartbeat sensing apparatus and illustrates how the threshold of the apparatus of FIG. 2 is caused to continuously increase during a single cardiac cycle.

The operations of the automatic sense threshold procedure are further illustrated by considering an exemplary sensed electrical signal shown in FIG. 5. At the end of the pacemaker ARP, the controller 100 resets the digital peak detector 70 via a reset signal at its input 70b. At this time, the controller 100 also stores in the threshold register 60 an initial low value by placing this value on the threshold control input 60a. This initial low value is set to slightly exceed the digitization noise level of the A/D converter 30. The sense output line 51 goes high whenever the input 50a from the digital absolute value circuit 40 is equal to or greater than the stored threshold value presented at the input 50b. The digital absolute value circuit 40 delivers a new sample to the digital comparator 51 regularly (e.g., every 2 ms). During a first pacemaker RRP, since the threshold value is arbitrarily low, the sense output line 51 of the digital comparator 50 is likely to go high. The pacemaker RRP is immediately restarted, as shown in FIG. 5. Because a finite time interval (e.g., 2 ms) occurs between samples, the sample value furnished to the comparator 50 is usually greater than or equal to the threshold value as long as the noise amplitude is increasing. Consequently, when the sense output 51 of the digital comparator 50 goes high, the peak value set in the peak detector 70 will exceed the threshold value by one or two digital quantization steps. (For example, if the samples from the digital absolute value circuit 40 can have values from 0 through 31, steps of value 1 would equal one quantization step.)

When the sense output 51 of digital comparator 50 goes high, the controller 100 sets the threshold register 60 to the new peak threshold value plus one. In the example shown in FIG. 5, after another 2 ms have elapsed, the next sample is similarly greater than the new threshold value. Although the digital absolute value circuit 40 rectifies the signal, it is shown in an unrectified form in FIG. 5 for purposes of clarity, so that the operations of the procedure can be keyed to the actual input signal. With a quantization noise level of 1, the initial threshold value TH1 (on the vertical axis of FIG. 5) is set equal to 4, a relatively low level which is nonetheless greater than the quantization noise level. The first machine RRP, RRP-1 in the drawing, begins at the end of the machine ARP. When the noise rises to the TH1 threshold level, the pacemaker RRP is restarted, shown by RRP-2. If the digital comparator 50 is triggered, then the peak output value at 70c must be 4 or greater at this time. In the example of FIG. 5, the peak value is equal to 4 so the controller 100 sets the new threshold to 5, which is the peak value plus 1. The threshold register 60 is increased each time the pacemaker RRP is retriggered. Eventually, in this example, RRP-19 is restarted and the sense output of the digital comparator 50 does not go high. The previous peak TH19 was, therefore, a measure of the peak noise detected during the extended pacemaker RRP. The controller then sets the threshold register 60 for sensing heartbeats rather than noise as a function of this peak noise value of TH19.

In one implementation, the heartbeat sensing threshold is set to the peak noise value plus a threshold increment value which has been determined as a function of the metabolic demand of a patient. The peak noise value defines the noise floor of the cardiac signal. The threshold increment is the amplitude of a cardiac signal, above that of the noise floor, which defines a natural heartbeat. If the patient is at rest as determined by metabolic demand measurement, the controller 100 sets a relatively large threshold increment value since attenuation of the signal voltage at the electrodes 11 and 12 due to exercise has not taken place. If the pacemaker determines by metabolic demand measurement that the patient is exercising, the controller 100 sets a smaller threshold increment value depending on the patient's metabolic demand. The more strenuously the patient is exercising, the lower the threshold increment value so long as the value is not smaller than a predetermined low limit.

In a second implementation, the controller 100 may average the peak heartbeat signal over a number of cardiac cycles and set the heartbeat sensing threshold between the peak noise value and the average heartbeat peak value. The position of the heartbeat sensing threshold between the peak noise value and the average heartbeat peak value is set to a metabolic-demand-dependent percentage increment. Thus, if the sensed metabolic demand indicates that the patient is not exercising, the controller 100 may set the heartbeat sensing threshold, for example, halfway between the peak noise value and the average heartbeat peak value. Since the amplitude of the input signal resulting from noise does not change with the patient's metabolic demand and the amplitude of the cardiac electrical signal is reduced when the patient's metabolic demand increases, the controller 100 reduces the percentage increment value accordingly. This provides for a smaller safety margin and more accurate sensing than is possible in prior art pacemakers that do not use a metabolic demand sensor to adjust sensitivity. If the patient is exercising with a peak metabolic demand, the controller 100 may set the heartbeat sensing threshold to the peak noise value plus 20% of the difference between the average heartbeat peak value and the peak noise value. Alternatively, in a third implementation, the heartbeat sensing threshold may be set according to metabolic demand and peak noise value without regard for the sensed heartbeat peak value. In this manner, the controller 100 may set the heartbeat sensing threshold to exceed the peak noise value by 75% of the peak noise value when the patient is at rest, and by 20% of its value while the patient exercises.

In a fourth implementation, the controller 100 may set the threshold close to the sensed heartbeat peak value, for example to 75% of the difference between the average heartbeat peak amplitude value and the peak noise value, and decrease the threshold as the patient's metabolic demand increases regardless of changes in the heartbeat peak amplitude.

In a fifth implementation, neither the gain nor the sense threshold is programmed, but rather the sensitivity may be set by automatically adjusting the gain via the procedure of the aforementioned third implementation and adjusting the sense threshold in the manner taught in the fourth implementation. Thus, there is shown a pacemaker for automatically adjusting sensing sensitivity as a function of a physiological sensor measurement to improve the accuracy of cardiac signal sensing when a patient is exercising. Accordingly, the pacemaker of the present invention automatically adjusts for smaller cardiac signals which occur while a patient is exercising so that the pacemaker may avoid undersensing of heartbeat signals and oversensing of noise, and may employ a smaller sensing threshold safety margin than is otherwise possible when the threshold is set either by programming, or via an automatic operation based on sensing of cardiac electrical signal characteristics. The automatic sensitivity adjustment of the present invention results in reduced oversensing of myopotentials and electromagnetic interference.

The improvement in cardiac signal sensing is shown in the following example: A pacemaker, either a prior art pacemaker or the pacemaker of the present invention, may fail to sense a heartbeat at the onset of exercise because the threshold is set too high. The prior art pacemaker will continue to undersense. The pacemaker of the present invention will decrement the threshold based on changes in the patient's metabolic demand alone and, as a result, restore sensing of natural heartbeats. Thus, the present invention allows the use of higher sensing thresholds which provide improved noise discrimination while continuing to sense true natural heartbeats.

Although various embodiments of a pacemaker sensing circuit for automatically adjusting sensitivity as a function of a measured metabolic demand have been described in accordance with the invention for the purpose of illustrating the manner of using the invention, it will be appreciated that the invention is not so limited. Accordingly, any and all modifications, variations or equivalent arrangements which may become apparent to those skilled in the art should be considered to be within the scope of the invention as defined in the appended claims. For example, although the described structural embodiment of the invention is a cardiac pacemaker, other devices which employ the sensing of cardiac signals, such as implantable defibrillators, cardioverters, antitachycardiac pacers, Holter monitors and the like, are to be considered within the scope of the invention. Furthermore, surface electrocardiograms in addition to endocardially-measured cardiac electrograms are to be considered sensed cardiac signals within the scope of the invention.

What is claimed is:

1. A patient heartbeat sensing apparatus comprising:
   first means for measuring a physiological parameter of the patient and for providing an output signal which is responsive to the patient's metabolic demand as indicated by the measured parameter;
   second means for sensing a signal which is responsive to cardiac activity and noise;

third means, having an adjustable sensitivity, for operating on said cardiac activity and noise signal, to determine therefrom the occurrence of a natural heartbeat; and fourth means for adjusting the sensitivity of said third means in response to said metabolic demand output signal, being responsive to increases in the patient's metabolic demand by increasing said sensitivity, and being responsive to decreases in the patient's metabolic demand by decreasing said sensitivity.

2. An apparatus according to claim 1, wherein:

said third and fourth means have a mode of operation of:

comparing signals from said second means against a variable sensing threshold value for determining the occurrence of a natural heartbeat; and setting said sensing threshold value
  (i) in response to increases in the patient's metabolic demand by decreasing said sensing threshold value, and
  (ii) in response to decreases in the patient's metabolic demand by increasing said sensing threshold value.

3. An apparatus according to claim 2, wherein:

said third and fourth means have a further mode of operation of:

setting said variable sensing threshold value to an initial threshold value in response to the occurrence of a heartbeat;

initiating the timing of a relative refractory period, and in response to said cardiac activity and noise signal exceeding said variable sensing threshold value during said relative refractory period, again initiating the timing of a relative refractory period and increasing the variable sensing threshold value, and in response to a lapse of such relative refractory period without said cardiac activity and noise signal exceeding said variable sensing threshold value, initiating the timing of a heartbeat sensing interval;

at the start of a heartbeat sensing interval setting the variable sensing threshold value as a function of both the variable sensing threshold value at the end of the preceding relative refractory period and the patient's metabolic demand; and in response to said cardiac activity and noise signal exceeding the variable sensing threshold value during a heartbeat sensing interval, determining that a heartbeat has occurred.

4. An apparatus according to claim 2, wherein:

said third and fourth means have a further mode of operation of:

in response to the detection of a natural heartbeat, deriving a value which is representative of the average of the peak amplitudes of the cardiac activity and noise signal during a preceding interval of time which is at least a few cardiac cycles long;

setting said variable sensing threshold value to an initial threshold value in response to the occurrence of a heartbeat;

initiating the timing of a relative refractory period;

in response to said cardiac activity and noise signal exceeding said variable sensing threshold value during said relative refractory period, again initiating the timing of a relative refractory period and increasing the variable sensing threshold value;

in response to a lapse of the relative refractory period without said cardiac activity and noise signal exceeding said variable sensing threshold value, initiating the timing of a heartbeat sensing interval;

at the start of a heartbeat sensing interval setting the variable sensing threshold value as a function of any of the three of:
  (i) the variable sensing threshold value at the end of the preceding relative refractory period,
  (ii) the average measured peak amplitude of the cardiac activity and noise signal, and
  (iii) the patient's metabolic demand, and in response to said cardiac activity and noise signal exceeding the variable sensing threshold value during a heartbeat sensing interval, determining that a heartbeat has occurred.

5. An apparatus according to claim 2, wherein:

said third and fourth means have a further mode of operation of:

setting said variable sensing threshold value to an initial threshold value in response to the occurrence of a heartbeat, and successively increasing said threshold value to a final value as the cardiac activity and noise signal increases, until the final threshold value represents the noise level in said cardiac activity and noise signal;

in response to said final threshold value representing the noise level in said cardiac activity and noise signal, initiating the timing of a heartbeat sensing interval;

at the start of a heartbeat sensing interval, setting a threshold value which is a function of both said final threshold level value and the patient's metabolic demand; and in response to said cardiac activity and noise signal exceeding said threshold value during a heartbeat sensing interval, indicating the occurrence of a heartbeat.

6. An apparatus according to claim 2, wherein:

said third and fourth means have a further mode of operation of:

in response to said third means detecting a natural heartbeat, measuring the peak amplitude of said cardiac activity and noise signal;

deriving a value representative of the average of the measured peak amplitudes of said cardiac activity and noise signal during a preceding time interval which is at least a few cardiac cycles long;

setting said variable sensing threshold value to an initial threshold value in response to the occurrence of a heartbeat, and successively increasing the threshold value to a final value as the cardiac activity and noise signal increases, until the final threshold value represents the noise level in said cardiac activity and noise signal;

in response to said final threshold value representing the noise level in said cardiac activity and noise signal, initiating the timing of heartbeat sensing interval;

at the start of a heartbeat sensing interval setting a threshold value which is a function of one or more of:
  (i) the final threshold level,
  (ii) the average measured peak amplitudes of said cardiac activity and noise signal, and
  (iii) the patient's metabolic demand, and in response to the cardiac activity and noise signal exceeding said threshold value during the timing of a heartbeat sensing interval, indicating the occurrence of a heartbeat.

7. An apparatus according to claim 1, wherein:
said third means includes means for amplifying said cardiac activity and noise signal;
said third and fourth means have a further mode of operation of:
in response to changes in the first means physiological parameter measurement, said fourth means selectively varies said third means for amplifying gain;
increasing said gain value in response to increase in the patient's metabolic demand; and
decreasing said gain value in response to decrease in the patient's metabolic demand.

8. An apparatus according to claim 7, wherein:
said third and fourth means have a further mode of operation of:
in response to the detection of a natural heartbeat by said third means, measuring the peak amplitude of said cardiac activity and noise signal;
deriving a value which is representative of the measured peak amplitudes of said cardiac activity and noise signal during a preceding time interval which is at least a few cardiac cycles long; and
adjusting said gain in response to said derived peak amplitude value.

9. An apparatus according to claim 8, wherein:
said third means includes
comparator means for comparing signals from said second means against a sensing threshold value for determining the occurrence of a natural heartbeat; and
said fourth means:
in response to increase in the patient's metabolic demand, decreases said sensing threshold value, and
in response to decrease in the patient's metabolic demand, increases said sensing threshold value.

10. An apparatus according to claim 9, wherein:
said third and fourth means have a further mode of operation of:
in response to the occurrence of a heartbeat, setting said variable sensing threshold value to an initial threshold value;
initiating the timing of a relative refractory period;
in response to said cardiac activity and noise signal exceeding said variable sensing threshold value during said relative refractory period, initiating again the timing of a relative refractory period, and increasing the variable sensing threshold value;
in response to the lapse of the relative refractory period without said cardiac activity and noise signal having exceeded said variable sensing threshold value, initiating the timing of a heartbeat sensing interval;
at the start of the heartbeat sensing interval, setting a variable sensing threshold value as a function of both:
(i) the variable sensing threshold value at the end of the preceding relative refractory period, and
(ii) the patient's metabolic demand; and
in response to said cardiac activity and noise signal exceeding the variable sensing threshold value during the timing of a heartbeat sensing interval, indicating the occurrence of a heartbeat.

11. An apparatus according to claim 9, wherein:
said third and fourth means have a further mode of operation of:
in response to the detection of a natural heartbeat by said third means measuring the peak amplitude of said cardiac activity and noise signal;
deriving a value representative of the average of the measured peak amplitudes of said cardiac activity and noise signal during a preceding time interval which is at least a few cardiac cycles long;
in response to the detection of a natural heartbeat setting said variable sensing threshold value to an initial threshold value;
initiating the timing of a relative refractory period;
in response to said cardiac activity and noise signal exceeding said variable sensing threshold value during said relative refractory period, initiating again the timing of a relative refractory period and increasing the variable sensing threshold value;
in response to the lapse of the relative refractory period without said cardiac activity noise signal exceeding said variable sensing threshold value, initiating a heartbeat sensing interval;
at the start of a heartbeat sensing interval, setting a variable sensing threshold value as a function of the three of:
(i) the variable sensing threshold value at the end of the preceding relative refractory period,
(ii) the average measured peak amplitude of the cardiac activity and noise signal, and
(iii) the patient's metabolic demand; and
in response to said cardiac activity and noise signal exceeding the variable sensing threshold value during a heartbeat sensing interval, indicating the occurrence of a heartbeat.

12. An apparatus according to claim 9, wherein:
said third and fourth means have a further mode of operation of:
in response to the occurrence of a heartbeat, setting said variable sensing threshold value to an initial threshold value and successively increasing the threshold value to a final value as the cardiac activity and noise signal increases until the final threshold value represents the noise level in said cardiac activity and noise signal;
in response to said final threshold value representing said noise level, initiating the timing of a heartbeat sensing interval;
at the start of a heartbeat sensing interval setting a threshold value which is a function of both:
(i) said final threshold level, and
(ii) the patient's metabolic demand, and
in response to the cardiac activity and noise signal exceeding said threshold value during the timing of a heartbeat sensing interval, indicating the occurrence of a heartbeat.

13. An apparatus according to claim 9, wherein:
said third and fourth means have a further mode of operation of:
in response to the detection of a natural heartbeat by said third means, measuring the peak amplitude of said cardiac activity and noise signal;
deriving a value representative of the average of the measured peak amplitudes of said cardiac activity and noise signal during a preceding time interval which is at least a few cardiac cycles long;
in response to the occurrence of a heartbeat, setting said variable threshold value to an initial threshold value and successively increasing the threshold value to a final value as the cardiac activity and noise signal increases, until the final threshold value represents the noise level in said cardiac activity and noise signal;

in response to said final value representing the noise level in said cardiac activity and noise signal, initiating the timing of a heartbeat sensing interval;

at the start of a heartbeat sensing interval setting a threshold value which is a function of the three of:
  (i) the final threshold level,
  (ii) the average measured peak amplitude of said cardiac activity and noise signal, and
  (iii) the patient's metabolic demand; and in response to the cardiac activity and noise signal exceeding said threshold value during a heartbeat sensing interval, indicating the occurrence of a heartbeat.

14. An apparatus according to claim 1, wherein: said third and fourth means have a further mode of operation of:
  in response to both the patient's metabolic demand being substantially stable and the detection of a natural heartbeat by said third means, measuring the peak amplitude of said cardiac activity and noise signal;
  deriving a value representative of the average of the measured peak amplitudes during a preceding time interval which is at least a few cardiac cycles long; and
  varying the sensitivity of said third means in response to said derived value.

15. A method of operating a patient heartbeat sensing apparatus, comprising:
  measuring a physiological parametr of the patient which is representative of the metabolic demand of the patient;
  sensing a signal which is representative of the cardiac electrical activity of the patient;
  adjusting the sensitivity of the apparatus to said sensed cardiac signal:
    (i) by increasing said sensitivity in response to a measured increase in said metabolic demand, and
    (ii) by decreasing said sensitivity in response to a measured decrease in said metabolic demand.

16. A method according to claim 15 wherein:
  said sensing of the cardiac signal includes comparing said cardiac signal to a sensing threshold value to determine whether or not said cardiac signal represents the occurrence of a natural heartbeat; and
  said sensitivity adjustment includes adjusting said sensing threshold value:
    (i) by decreasing said sensing threshold value to increase said sensitivity, and
    (ii) by increasing said sensing threshold value to decrease said sensitivity.

* * * * *